United States Patent

Golan et al.

[11] Patent Number: 6,136,280
[45] Date of Patent: Oct. 24, 2000

[54] AUTOCLAVE DEVICE AND PTC HEATING ARRANGEMENT FOR USE THEREWITH

[75] Inventors: Gad Golan, Hod Hasharon; Yuly Galperin, Holon, both of Israel

[73] Assignee: Body Heat Ltd., Ariel, Israel

[21] Appl. No.: 09/055,286

[22] Filed: Apr. 6, 1998

[51] Int. Cl.[7] .................................................. A61L 2/00
[52] U.S. Cl. .................... 422/295; 219/201; 219/385; 219/481; 219/520; 219/530; 219/531; 219/536; 219/543; 422/297; 422/307
[58] Field of Search .................... 422/295, 297, 422/307; 219/201, 385, 401–403, 405, 409, 410, 481, 520, 530, 531, 536, 543; 338/22 R, 23

[56] References Cited

U.S. PATENT DOCUMENTS

| | | | |
|---|---|---|---|
| 4,529,868 | 7/1985 | Bowen | 215/521 |
| 4,677,280 | 6/1987 | Kai | 219/385 |
| 5,520,892 | 5/1996 | Bowen | 422/295 |

*Primary Examiner*—Krisanne Thornton
*Attorney, Agent, or Firm*—Nixon & Vanderhye P.C.

[57] ABSTRACT

An autoclave type sterilization device which includes an autoclave sterilization chamber with an electrical heating arrangement mounted thereon. This electrical heating arrangement employs one or more positive temperature coefficient (PTC) thermistors as heating elements. These heating elements are in direct thermal and electrical contact on opposing sides, which are coated with a conductive metal such as aluminum, with electrodes to supply electrical current. These electrodes are, in turn, in direct thermal contact on their outward-facing sides with respect to the heating elements with plates which are formed of a thermally conductive and electrically insulating ceramic material such as $AL_2O_3$, and the plates are in direct thermal contact on their outward-facing sides with respect to the heating elements with heat radiation units which include heat transfer portions which are fabricated to engage and are in direct thermal contact with a portion of the wall of the autoclave chamber. The heating elements are positioned by an electrically and thermally insulating frame made of heat-resistant material which serves, together with the heat radiation units, to fully enclose the heating elements. The heat radiation units further are in thermal and mechanical contact with each other which, together with the abovementioned enclosure of the heating elements, protects them from thermal gradients due to unbalanced heat transfer or exposure to air or gas flow and hence, from the known "pinch effect."

18 Claims, 4 Drawing Sheets

AUTOCLAVE DEVICE AND PTC HEATING ARRANGEMENT FOR USE THEREWITH

FIELD OF THE INVENTION

The present invention relates to autoclaves and to electrical heating devices therefor, particularly those employing thermistors with positive temperature coefficient of resistance (PTC) as heating elements.

BACKGROUND OF THE INVENTION

In medicine, sterilization of instruments is known to be commonly required before they can be safely allowed to come into contact with patients. The same is true of other tools and even drugs and linens. Sterilization is also required in other fields such as biology, pharmacology, and veterinary medicine. It is typically performed in a pressurized chamber such as in an autoclave by producing steam from distilled or mineral-free water and heating it. In a typical sterilization cycle, steam temperatures of 137° C. and pressures of up to 3 bars are achieved and maintained for a predetermined number of minutes.

Exemplary of current art are autoclaves manufactured by Tutnauer U.S.A. Co. Ltd., which use electric heaters mounted on the external surface of the autoclave cylindrical chamber using bolted connections. The heating elements in the heaters are nickel-chromium wire which are mounted on a flat micanite framework with two micanite insulating liners enclosed in an aluminum cladding which is in thermal contact with the external surface of the autoclave cylindrical chamber.

In a typical sterilization cycle, electrical current is passed through the nickel-chromium wire which produce heat which is transferred through the micanite liners to the aluminum cladding and therefrom to the external surface of the autoclave chamber. The chamber, which has been sealed with the items to be sterilized an a necessary quality of distilled or mineral-free water, heats until the water is evaporated to steam and the required temperature and pressure are achieved. When the sterilization cycle is completed, clean, dry air is circulated in the chamber to cool and dry the chamber and its contents.

These heaters have a number of disadvantages. They are inefficient because of the high thermal resistance of the micanite, the large contact surfaces between the nickel-chromium wire and the micanite liners, between the liners and the aluminum cladding, and between the cladding and the autoclave chamber surface, and because only one side of the heater contacts the chamber for heat transfer thereto. A further problem with single-sided heat transfer is the risk of overheating on the other side since there is no direct removal of heat therefrom. Overheating of the entire heater unit is also possible in the absence of sufficient water in the chamber. This requires temperature limiters, such as thermostats and power controllers which make the entire autoclave more complicated, more expensive, and less reliable.

U.S. Pat. No. 5,520,892 discloses sterilization unit for dental and other instruments which employs thermistors with positive temperature coefficient of resistance (PTC) as heating elements. The are self regulating with respect to temperature, thereby eliminating the above-mentioned overheating problems. The unit disclosed employs two-stage heating to provide very precise temperature regulation and has other features required in certain specific applications. It also has a relatively small chamber for objects to be sterilized.

U.S. Pat. Nos. 4,677,280 and 4,529,868 also disclose sterilization units employing PTC heating elements, but both of these are very specifically applied to sterilization of contact lenses.

None of the above devices are applicable to the full range of sizes and types of sterilization units and none can be fitted as heaters on existing autoclave units.

SUMMARY OF THE INVENTION

The present invention seeks to provide an autoclave type sterilization device, which overcomes disadvantages of known art by employing improved positive temperature coefficient (PTC) thermistor heating arrangements. The heating arrangements of the present invention include radiation members in thermal contact with both sides of the PTC heating elements which are both in thermal contact with the surface of the autoclave chamber thereby providing faster and more efficient heating than prior art devices.

The present invention further seeks to provide heating arrangements based on positive temperature coefficient (PTC) thermistors useful for retrofitting existing autoclave type sterilization devices.

Accordingly, there is provided, in accordance with a preferred embodiment of the invention, an autoclave type sterilization device which includes an autoclave sterilization chamber with an electrical heating arrangement mounted thereon. This electrical heating arrangement employs one or more positive temperature coefficient (PTC) thermistors as heating elements. These heating elements are in direct thermal and electrical contact on opposing sides, which are coated with a conductive metal such as aluminum, with electrodes to supply electrical current. These electrodes are, in turn, in direct thermal contact on their outward-facing sides with respect to the heating elements with plates which are formed of a thermally conductive and electrically insulating ceramic material such as $AL_2O_3$, and the plates are in direct thermal contact on their outward-facing sides with respect to the heating elements with heat radiation units which include heat transfer portions which are fabricated to engage and are in direct thermal contact with a portion of the wall of the autoclave chamber. The heating elements are positioned by an electrically and thermally insulating frame made of heat-resistant material which serves, together with the heat radiation units, to fully enclose the heating elements. The heat radiation units further are in thermal and mechanical contact with each other which, together with the abovementioned enclosure of the heating elements, protects them from thermal gradients due to unbalanced heat transfer or exposure to air or gas flow and hence, from the known "pinch effect."

The internal elements of the heating arrangement are further held in place and in good thermal contact with each other by mechanical pressure and by a thermally and electrically conductive adhesive. The insulating plates are coated on their inward-facing with respect to the heating elements with a conductive metal such as aluminum to provide good thermal contact therewith. The conductive coatings on the insulating plates serve as the electrodes for the electrical heating arrangement.

There is further provided, in accordance with a further preferred embodiment of the invention, a heating arrangement as described above which can be mounted on an existing autoclave chamber in place of prior art heating arrangements.

BRIEF DESCRIPTION OF THE DRAWINGS

The present invention will be more fully understood and appreciated from the following detailed description taken in conjunction with the drawings, in which.

DETAILED DESCRIPTION OF THE INVENTION

Figure 1A:
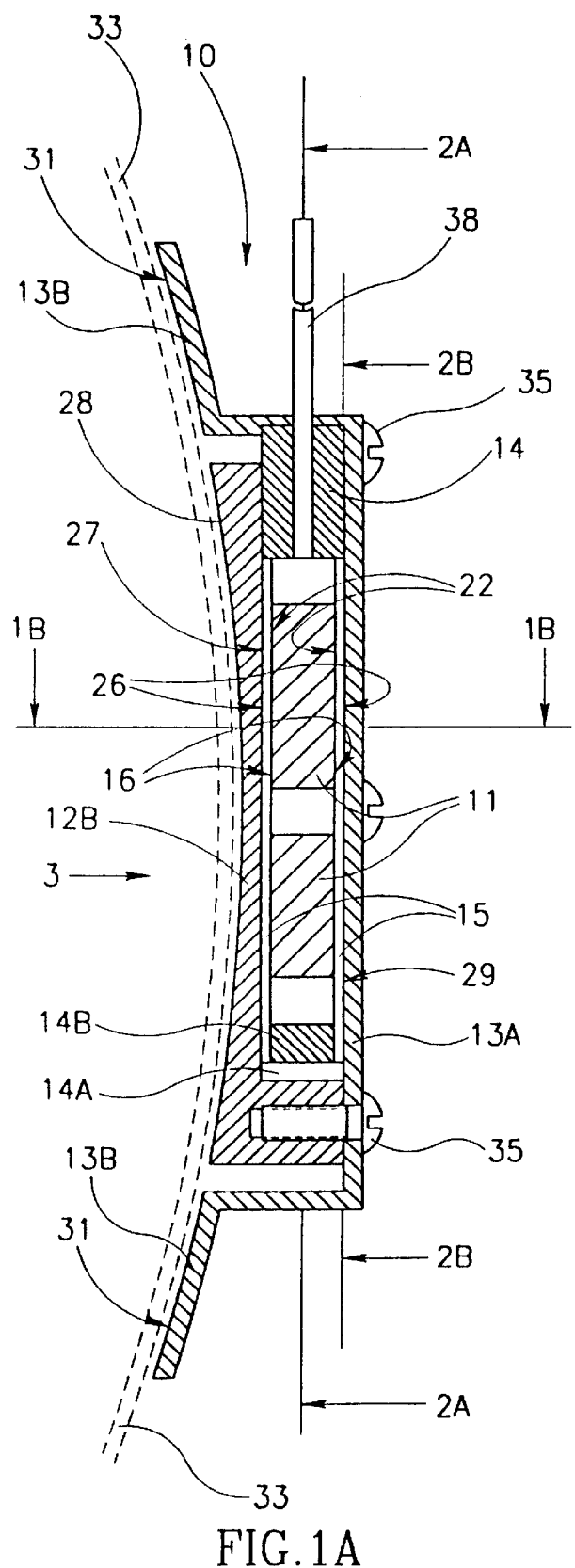
FIG. 1A is a schematic side-sectional view of an electrical heating device for an autoclave type sterilization device constructed and operative in accordance with a preferred embodiment of the present invention.
Figure 1B:
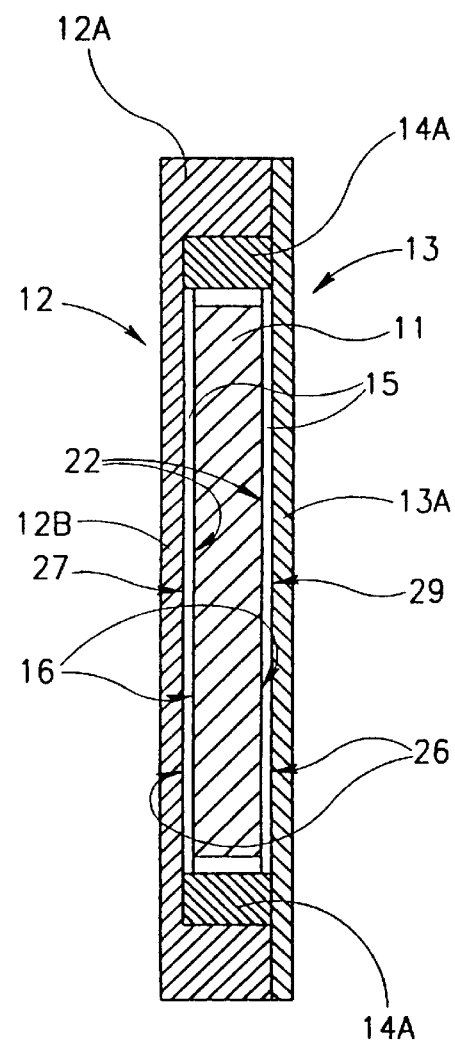
FIG. 1B is a cross-sectional view of the electrical heating device of FIG. 1A, taken along the line B—B therein.

Referring now to FIGS. 1A and 1B, there is shown an electrical heating device referred to generally as 10, for use in a heating arrangement for use with an autoclave type sterilization device, constructed and operative in accordance with a preferred embodiment of the present invention. Electrical heating device 10 preferably has an array of one or more heating elements 11 which are positive temperature coefficient (PTC) thermistors. They are fabricated with preferably parallel, generally flat, surfaces on opposing faces 22, which are coated with metallized, preferably by provision of a coating of a conductive metal such as aluminum, to serve as thermal and electrical contact surfaces. On opposing sides of heating elements 11 are plates 15 which are formed of a thermally conductive and electrically insulating ceramic material such as $AL_2O_3$. Inward-facing surfaces 16 of insulating plates 15 are coated with a conductive metal such as aluminum, thereby constituting thermal and electrical contact surfaces.

In a preferred embodiment of the present invention, there coated surfaces 16 of insulating plates 15 serve as electrodes for heating device 10, for supplying electrical current to heating elements 11 thereby.

Disposed on outward-facing surfaces 26 of insulating plates 15 and in direct thermal contact therewith are two heat radiator units, referred to generally as 12 and 13, shown in FIGS. 1A and 1B. Radiator 12 and 13 are made of a material that is a good material and electrical conductor, such as aluminum. First radiator unit 12 has an enclosing portion 12A that surrounds heating elements 11 and insulating plates 15 on their sides other than their generally parallel, flat, contact surfaces and, integrally joined therewith, a heat transfer portion 12B which has one generally flat, inward-facing, contact surface 27 in thermally conductive contact with the outward-facing surface of one of insulating plates 15 and a second outward-facing contact 28 fabricated to match the shape of a portion of the outer wall 33 of the autoclave chamber and in thermally conductive contact therewith. In the present preferred embodiment, wherein the autoclave chamber is cylindrical, the outward-facing contact surface 28 of heat transfer portion 12B of first radiator unit 12 is concave and has the same radius as that of the convex outer wall 33 of the autoclave chamber. Second radiator unit 13 has a plate portion 13A which has one generally flat, inward-facing, contact surface 29 in thermally conductive contact with the outward-facing surface of the second of insulating plates 15 and, integrally joined therewith, in the present embodiment, two heat transfer portions 13B having outward-facing contact surfaces 31 fabricated to match the shape of a portion of the outer wall 33 of the autoclave chamber and in thermally conductive contact therewith similar to outward-facing contact surface 28 of heat transfer portion 12B of first radiator unit 12. Plate portion 13A of second radiator unit 13 is also in thermally conductive contact with enclosing portion 12A of first radiator unit 12.

In the above description, the best conduction between all surfaces described as being in thermally-conductive contact with each other is improved by the use of a thermally and electrically conductive adhesive, such as Ceramabond™ 5526, a high-temperature adhesive produced by Aremco Products, Inc. of Ossining, N.Y. 10562, U.S.A., applied therebetween.

PTC thermistor heating elements 11 convert electrical energy applied thereto to thermal energy. Radiator units 12 and 13 are fabricated so that their masses and the surface areas of heat transfer portions 12B and 13B allow thermal energy removal from both sides of PTC heating elements 11 via plates 15 and its transfer to outer wall 33 of the autoclave chamber at generally equal rates. This and the fact that the two radiator units 12 and 13 are in thermal contact with each other ensures that temperature on both sides of PTC heating elements 11 will be the same thereby protecting PTC heating elements 11 from the known "pinch effect" and increasing their efficiency, reliability, and durability.

Figure 2A:
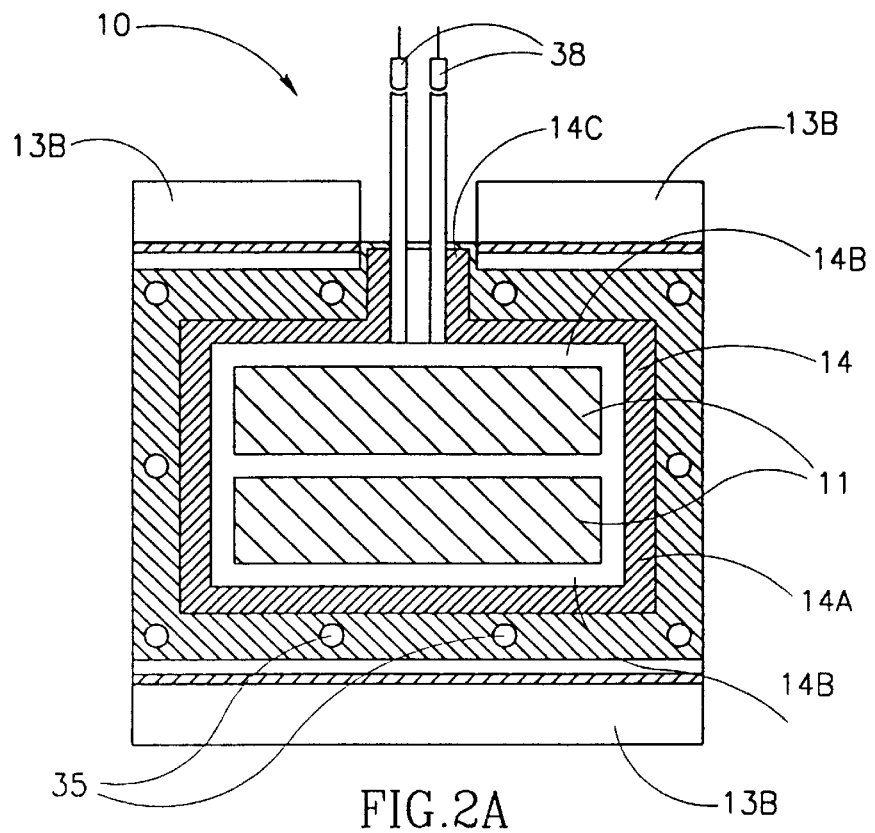
FIG. 2A is a side-sectional view of the electrical heating device of FIG. 1A, taken along the line 2A—2A therein.
Figure 2B:
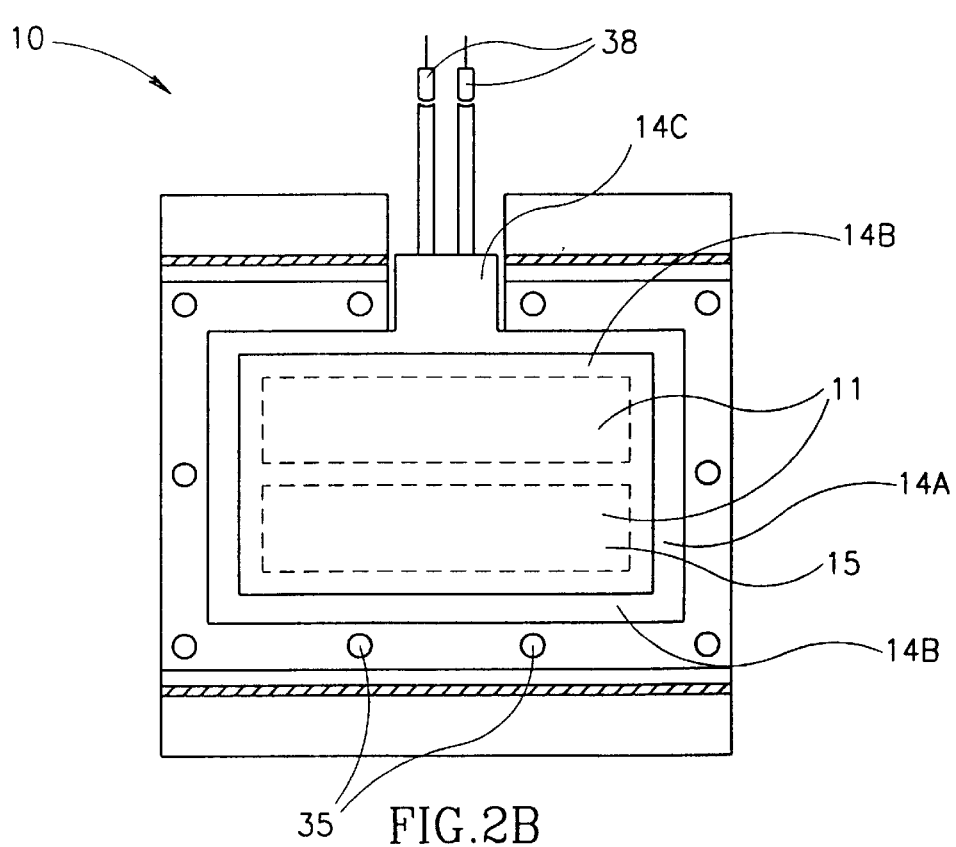
FIG. 2B is a side-sectional view of the electrical heating device of FIG. 1A, taken along the line 2B—2B therein.

Referring now to FIGS. 2A and 2B, there are shown two side-sectional views of electrical heating device 10 as shown in FIG. 1A, taken along lines Q—Q and R—R therein, respectively. An array of PTC heating elements 11 are positioned by an electrically and thermally insulating frame 14 made of heat-resistant material. Frame 14 has flanges 14A on either side of heating elements 11, and end pieces 14B and a conduit 14C for wires 38 with heat-resistant insulation which supply electrical current to heating device 10. The view seen in FIG. 2B is taken through insulating plate 15 which is in electrical and thermal contact with heating elements 11 at contact surface 22 on one side thereof (FIG. 1B).

It can be seen from FIG. 2A that flanges 14A and end pieces 14B and conduct 14C of positioning frame 14 surround the array of the heating element 11 on four sides. Referring again to FIG. 1A, the top flange 14A of positioning frame 14, shown partially cut away, can be seen to enclose the array of heating elements 11 from above, as drawn. Heating elements 11 are enclosed by positioning frame 14 which is enclosed by radiator units 12 and 13 as described above. Radiators 12 and 13 are joined mechanically by bolts 35.

Figure 3:
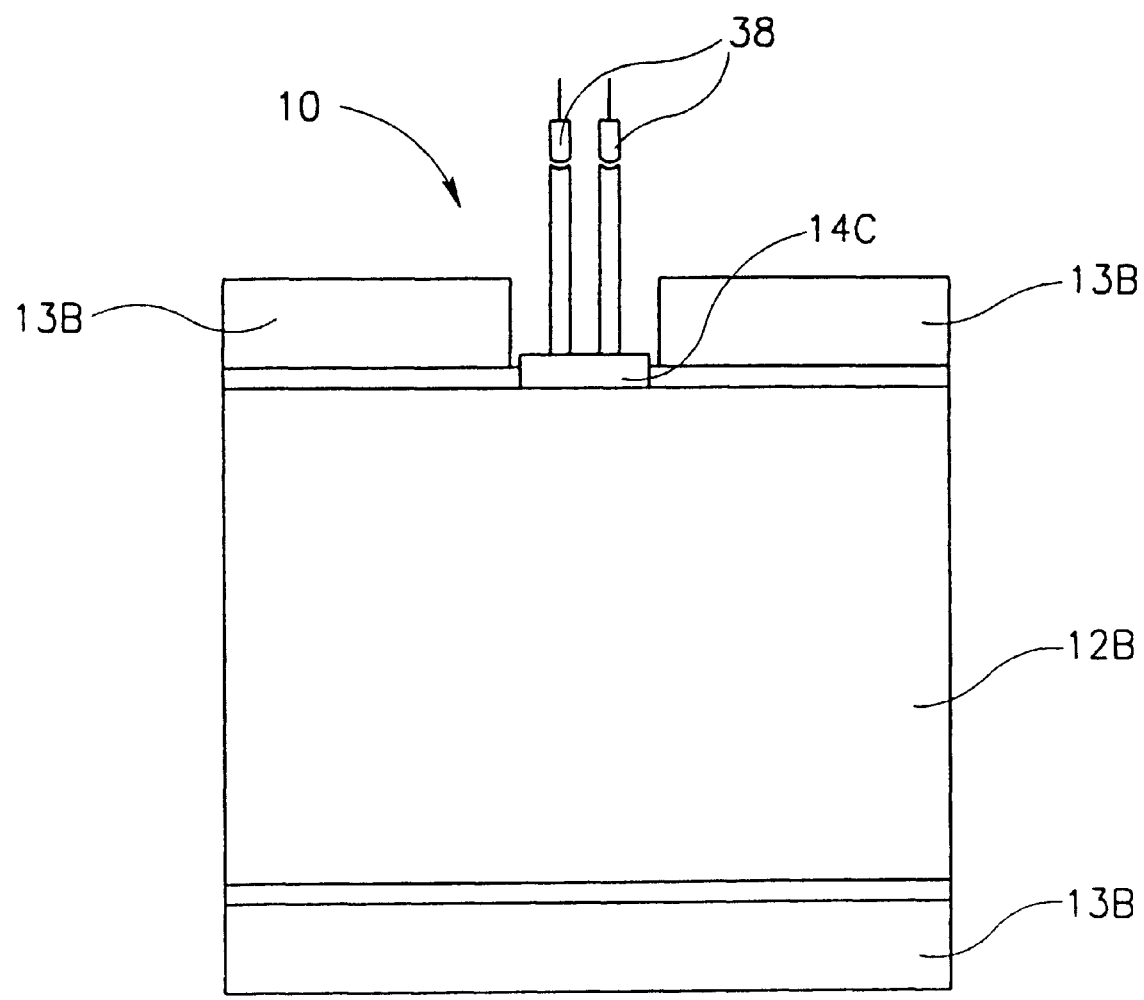
FIG. 3 is a front view of the electrical heating device of FIG. 1A, taken in direction of the arrow 3 therein.

Referring now to FIG. 3, there is shown a front view of electrical heating device 10, constructed in accordance with a preferred embodiment of the present invention. In this view there are seen outward-facing contact surfaces (28 and 31 in FIG. 1A) of heat transfer portions 12B and 13B of radiators 12 and 13 that are in thermal contact with a portion of the outer wall (33 in FIG. 1A) of the autoclave chamber.

Figure 4A:
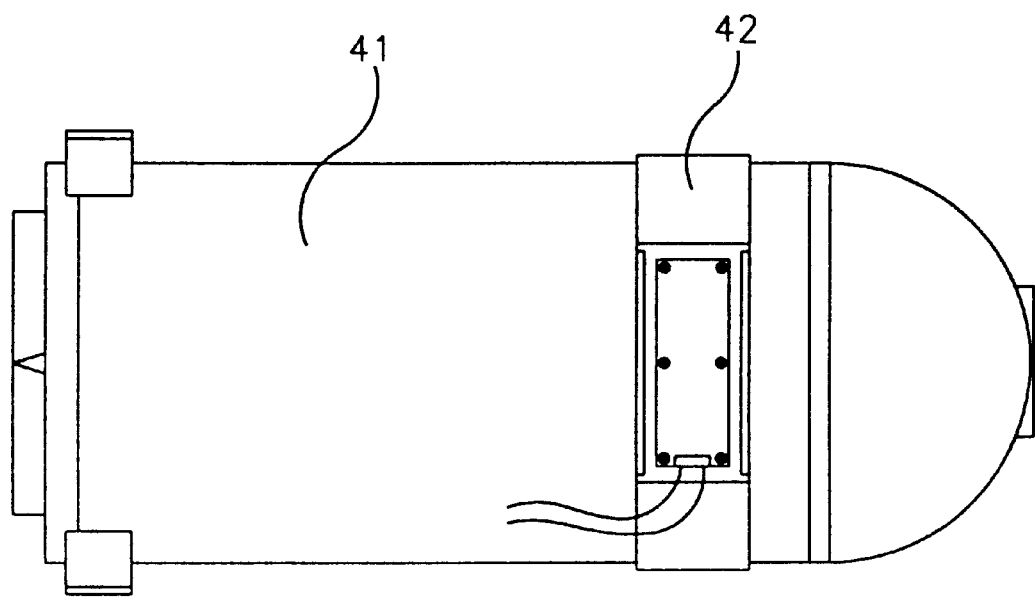
FIGS. 4A and 4B are bottom and top views, respectively, of an autoclave chamber with a heater unit based on a preferred embodiment of the present invention mounted thereon.
Figure 4B:
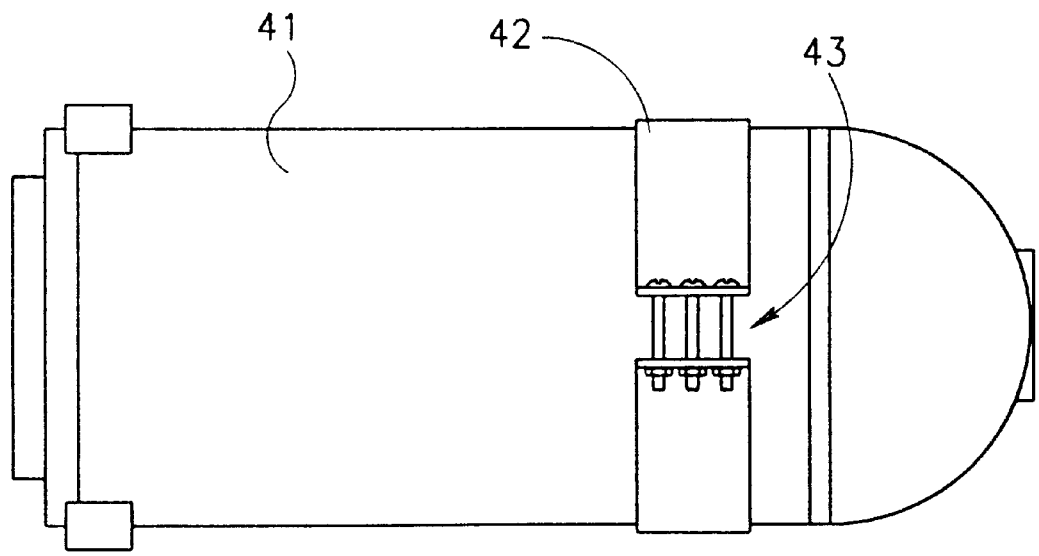

Referring now to FIGS. 4A and 4B, there is shown a typical autoclave chamber with a heater unit 42 constructed in accordance with a preferred embodiment of the present invention, in bottom and top views, respectively. Since unevaporated water will sit in the bottom of the autoclave chamber, heater unit 42 is mounted on the bottom side of autoclave chamber 41 thereby to deliver maximum heating to the water therein. Bolted connection 43 secures the heater in place and ensures good thermal contact between heater unit 42 and wall of autoclave chamber 41. This may be a mounting similar to that used in the prior art. It will thus be appreciated hat existing autoclave chambers can be retrofitted with heater units based on embodiments of the present invention with suitably fabricated heat exchange portions, such as those denoted 12B and 13B, in FIG. 1A for engaging the outer surface of the autoclave chamber.

It will be further appreciated, by persons skilled in the art that the scope of the present invention is not limited by what has been specifically shown and described hereinabove, merely by way of example. Rather, the scope of the present invention is defined solely by the claims, which follow.

We claim:

1. An autoclave type sterilization device which includes:
   an autoclave chamber for sterilization of objects when suitable liquid introduced therein is brought to suitable temperature and pressure,
   at least one electrical heating device arranged in thermal contact with the outer surface of said autoclave chamber; and
   mounting means for positioning said at least one electrical heating device on said outer surface of said autoclave chamber and for maintaining thermal contact therebetween;
   wherein said at least one electrical heating device includes:
      at least one positive temperature coefficient (PTC) thermistor heating element having generally parallel, flat, contact surfaces;
      a pair of plate members formed of an electrically insulating and thermally conductive material having generally parallel, flat, inward- and outward-facing contact surfaces and wherein said inward-facing contact surfaces are coated with a thermally and electrically conductive metal;
      a pair of heat radiation members formed of an electrically and thermally conductive material, wherein first heat radiation member includes:
         an enclosing portion surrounding said at least one positive temperature coefficient (PTC) thermistor heating element on their sides other than their generally parallel, flat, contact surfaces and
         a heat transfer portion having a generally flat, inward-facing, contact surface for thermally conductive contact with the first of said outward-facing contact surfaces of said plate members and with an outward-facing contact surface fabricated to engage a portion of said outer surface of said autoclave chamber for thermally conductive contact thereby to define a thermal interface therewith; and
      second heat radiation member comprises:
         a plate portion having a generally flat, inward-facing, contact surface for thermally conductive contact with the second of said outward-facing contact surfaces of said plate members and
         at least one heat transfer portion with outward-facing contact surfaces fabricated to engage portions of said outer surface of said autoclave chamber for thermally conductive contact thereby to define thermal interfaces therewith;
      electrode means disposed about said at least one heating element operative to provide thermally and electrically conductive contact with said contact surfaces thereof and thermally conductive contact with said inward-facing contact surfaces of said plate members;
      means for fastening said heat radiation members about said plate members such that said inward-facing, contact surfaces of said plate portions are held in thermally conductive contact with said outward-facing contact surfaces of said plates members thereby to define therewith thermal interfaces,
      said means for fastening being further operative to fasten said plate members about said electrode means and said electrode means about said at least one heating element such that said inward-facing, contact surfaces of said plate members are held in electrically and thermally conductive contact with said electrode means and said electrode means are held in electrically and thermally conductive contact with said flat contact surfaces of said at least one heating element thereby to define therewith thermoelectric interfaces;
      enclosing means formed of an electrically and thermally insulating material and formed for positioning around said at least one heating element and between said plate portions of said heat radiation members so as to prevent a flow of gas from coming into contact with said at least one heating element; and
      terminal means attached to said electrode means, operative to permit flow of electric current therethrough, across said interfaces, and via said at least one heating element, thereby producing thermal energy therein;
   wherein, when an electrical current passes through said electrical heating device, thermal energy from said at least one heating element is conducted across said interfaces to said heat radiation members and thereby to said autoclave chamber thereby heating the contents thereof.

2. An autoclave type sterilization device according to claim 1 wherein said contact surfaces of said at least one heating element are coated with a thermally and electrically conductive metal.

3. An autoclave type sterilization device according to claim 1 wherein said contact surfaces of said at comprises said metal-coated inward-facing surfaces of said plate members.

4. An autoclave type sterilization device according to claim 1 wherein said means for fastening comprises compression means.

5. An autoclave type sterilization device according to claim 1 wherein said means for fastening comprises an adhesive which is electrically and thermally conductive applied to all said contact surfaces of all said interfaces.

6. An autoclave type sterilization device according to claim 1 wherein said terminal means comprises heat-resistant wires.

7. An autoclave type sterilization device according to claim 1 wherein said enclosing means comprises a positioning frame and a pair of flanges.

8. An autoclave type sterilization device according to claim 7 wherein said at least one heating element comprises at least two heating elements and said enclosing means further comprises spacing members operative to position said at least two heating elements so as to prevent touching contact therebetween.

9. An autoclave type sterilization device according to claim 1 wherein said enclosing portion and said plate portion of said pair of heat radiation members are in thermal and mechanical contact.

10. For use with an autoclave chamber for sterilization of objects, an electrical heating arrangement which includes:

at least one electrical heating device arranged in thermal contact with the outer surface of an autoclave chamber and mounting means for positioning said at least one electrical heating device on the outer surface of an autoclave chamber and for maintaining thermal contact therebetween;

wherein said at least one electrical heating device includes:

at least one positive temperature coefficient (PTC) thermistor heating element having generally parallel, flat, contact surfaces;

a pair of plate members formed of an electrically insulating and thermally conductive material having generally parallel, flat, inward- and outward-facing contact surfaces and wherein said inward-facing contact surfaces are coated with a thermally and electrically conductive metal;

a pair of heat radiation members formed of an electrically and thermally conductive material, wherein first heat radiation member includes:

an enclosing portion surrounding said at least one positive temperature coefficient (PTC) thermistor heating element on their sides other than their generally parallel, flat, contact surfaces and a heat transfer portion having a generally flat, inward-facing, contact surface for thermally conductive contact with the first of said outward-facing contact surfaces of said plate members and with an outward-facing contact surface fabricated to engage a portion of the outer surface of the autoclave chamber for thermally conductive contact thereby to define a thermal interface therewith; and second heat radiation member comprises:

a plate portion having a generally flat, inward-facing, contact surface for thermally conductive contact with the second of said outward-facing contact surfaces of said plate members and at least one heat transfer portion with outward-facing contact surfaces fabricated to engage portions of the outer surface of the autoclave chamber for thermally conductive contact thereby to define thermal interfaces therewith;

electrode means disposed about said at least one heating element operative to provide thermally and electrically conductive contact with said contact surfaces thereof and thermally conductive contact with said inward-facing contact surfaces of said plate members;

means for fastening said heat radiation members about said plate members such that said inward-facing, contact surfaces of said plate portions are held in thermally conductive contact with said outward-facing contact surfaces of said plates members thereby to define therewith thermal interfaces, said means for fastening being further operative to fasten said plate members about said electrode means and said electrode means about said at least one heating element such that said inward-facing, contact surfaces of said plate members are held in electrically and thermally conductive contact with said electrode means and said electrode means are held in electrically and thermally conductive contact with said flat contact surfaces of said at least one heating element thereby to define therewith thermoelectric interfaces;

enclosing means formed of an electrically and thermally insulating material and formed for positioning around said at least one heating element and between said plate portions of said heat radiation members so as to prevent a flow of gas from coming into contact with said at least one heating element; and terminal means attached to said electrode means, operative to permit flow of electric current therethrough, across said interfaces, and via said at least one heating element, thereby producing thermal energy therein;

wherein, when an electrical current passes through said electrical heating device, thermal energy from said at least one heating element is conducted across said interfaces to said heat radiation members and thereby to said autoclave chamber thereby heating the contents thereof.

11. An electrical heating arrangement according to claim 10 wherein said contact surfaces of said at least one heating element are coated with a thermally and electrically conductive metal.

12. An electrical heating arrangement according to claim 10 wherein said electrode means comprises said metal-covered inward-facing surfaces of said plate members.

13. An electrical heating arrangement according to claim 10 wherein said means for fastening comprises compression means.

14. An electrical heating arrangement according to claim 10 wherein said means for fastening comprises an adhesive which is electrically and thermally conductive applied to all said contact surfaces of all said interfaces.

15. An electrical heating arrangement according to claim 10 wherein said terminal means comprises heat-resistant wires.

16. An electrical heating arrangement according to claim 10 wherein said enclosing means comprises a positioning frame and a pair of flanges.

17. An electrical heating arrangement according to claim 16 wherein said at least one heating element comprises at least two heating elements and said enclosing means further comprises spacing members operative to position said at least two-heating elements so as to prevent touching contact therebetween.

18. An electrical heating arrangement according to claim 10 wherein said enclosing portion and said plate portion of said pair of heat radiation members are in thermal and mechanical contact.

* * * * *

UNITED STATES PATENT AND TRADEMARK OFFICE
CERTIFICATE OF CORRECTION

PATENT NO.    : 6,136,280
DATED         : October 24, 2000
INVENTOR(S)   : Golan et al.

It is certified that error appears in the above-identified patent and that said Letters Patent is hereby corrected as shown below:

<u>Title page,</u>
Item [30], Foreign Priority Application, add -- Israel IL 122833, 12/31/97 --

Signed and Sealed this

Sixth Day of August, 2002

Attest:

Attesting Officer

JAMES E. ROGAN
*Director of the United States Patent and Trademark Office*